United States Patent [19]

Brillhart et al.

[11] Patent Number: 5,198,250
[45] Date of Patent: Mar. 30, 1993

[54] FOOD AND PHARMACEUTICAL COMPOSITIONS CONTAINING SHORT CHAIN MONOUNSATURATED FATTY ACIDS AND METHODS OF USING

[75] Inventors: Donald D. Brillhart, Cleveland; Gerald L. Maurer, Cincinnati, both of Ohio

[73] Assignee: Lipotech Partners Limited Partnership, Cleveland, Ohio

[21] Appl. No.: 552,588

[22] Filed: Jul. 16, 1990

[51] Int. Cl.$^5$ .......................... A23K 1/00; A23L 1/00
[52] U.S. Cl. ....................................... 426/2; 426/601; 514/560
[58] Field of Search ...................... 426/2, 601; 514/560

[56] References Cited

U.S. PATENT DOCUMENTS 4,472,432  9/1984  Iwamura et al. .................... 424/318

FOREIGN PATENT DOCUMENTS 2140688  12/1984  United Kingdom .

OTHER PUBLICATIONS

"Baileys Industrial Oil and Fat Products" vol. 1 4th edition Daniel Swern Editor John Wiley Publisher (1980) pp. 26-31.
Bonanome, Andrea and Grundy, Scott M., "Effects of Dietary Fats on Plasma Cholesterol in Humans" *Reciprocal Meat Conference Proceedings*, vol. 40, 1987 pp. 89-91.
Grundy, Scott M., M.D., PhD. "Comparison of Monounsaturated Fatty Acids and Carbohydrates for Lowering Plasma Cholesterol", *The New England Journal of Medicine*, vol. 311 No. 12, Mar. 20, 1986, pp. 745-748.
Grundy, Scott M., M.D., Ph.D. "Monounsaturated Fatty Acids, Plasma Cholesterol, and Coronary Heart Disease" Am. J. Clin. Nutr. 1987:45 pp. 1168-1175.
Iemori, Yukio et al., "Pharmaceuticals for the Activation of Brain Metabolism" *Chemical Abstracts*, vol. 105, 1986 No. 49086h, p. 397.
Mattson, Fred H. and Grundy, Scott M. "Comparison of Effects of Dietary Saturated, Monounsaturated, and Polyunsaturated Fatty Acids on Plasma Lipids and Lipoproteins in Man" *Journal of Lipid Research*, vol. 26, 1985, pp. 194-203.
Mensink, Ronald P. and Katan, Martijn B., "Effect of Monounsaturated Fatty Acids Versus Complex Carbohydrates on High-Density Lipoproteins in Healthy Men and Women" *The Lancet*, Jan. 17, 1987 pp. 122-125.
Yamori, Yukio; Nara, Yasuo; Tsubouchi, Toshinori; Sogawa, Yoshori; Ikeda, Katsumi and Horie, Ryoichi, "Dietary Prevention of Stroke and its Mechanisms in Stroke-Prone Spontaneously Hypertensive Rats-Preventive Effect of Dietary Fibre and Palmitoleic Acid" *Journal of Hypertension*, 1986, vol. 4 (suppl 3) pp. S449-S452.
Abraham et al., The American Journal of Cardiology, "Adipose Fatty Composition ... " pp. 269-272, vol. 63, 1989.
Beuchat and Worthington, J. Food Technol., "Fatty Acid Composition of Tree Nut Oils", pp. 355-358, vol. 13, 1978.
Chan, ed. *Handbook of Tropical Foods*, "Macadamia Nuts", Cavaletto, pp. 361, 369-375, ch. 9, 1983.
Cotran, Kumar & Robbins, *Robbins Pathologic Basis of Disease*, "Blood Vessels", pp. 556-579, ch. 12, 1989.
Emken, Journal American Oil Chemists Soc., "Biochemistry of Unsaturated Fatty Acid Isomers", pp. 995-1004, vol. 60 No. 5, 1983.
Grundy, American Journal Nutrition, "Monounsaturated Fatty Acids and Cholesterol Metabolsim ... ", pp. 529-533, 1989.
Guyton, *Textbook of Medical Physiology* (4th Edition) "Lipid Metabolism", pp. 799-811, ch. 68, 1971.
MacFarlane and Harris, *Journal American Oil Chemists Soc.* Monograph, "Macadamia Nuts as an Edible Oil Source", pp. 103-108, 1981.
Manganaro, et al., Lipids, "Acylglycerol Structure of Genetic Varieties of Peanut Oils ... " pp. 508-517, vol. 16, No. 7, 1981.
Parthasarathy, et al., Proc. Natl. Acad. Sci., "Low Density Lipoprotein Rich in Oleic Acid", pp. 3894-3898, vol. 87, 1990.
Reeves and Weihrauch, U.S.D.A. Handbook No. 8-4, "Composition of Foods: Fats and Oils", pp. 15-17, 21, 1979.
Schiff, ed. *Diseases of the Liver* (5th Edition), "Fatty Liver", Alpers and Sabesin, pp. 813-845, ch. 22, 1982.
Spady and Dietschy, Proc. Natl. Acad. Sci., "Dietary Saturated Triacylglycerols ... ", pp. 4526-4530, 1985.
Stein, ed. *Internal Medicine* (2nd Edition), "Disorders of Lipids and Lipoproteins", Grundy, pp. 2035-2050 ch. 302, 1987.
Weihrauch, U.S.D.A. Human Nutrition Information Service, "Provisional Table on the Fatty Acid and Cholesterol Content of Selected Foods", 1984.
Halliwell and Gutteridge, *Free Radicals in Biology and Medicine* (2nd Ed.), "Lipid Peroxidation", pp. 188-267, ch. 4, 1984.

*Primary Examiner*—R. B. Penland
*Attorney, Agent, or Firm*—Wood, Herron & Evans

[57] ABSTRACT

Food and pharmaceutical compositions are disclosed which contain amounts of short chain monounsaturated fatty acids or their derivatives sufficient to increase the content of the fatty acids within the tissues when said compositions are administered and to substantially improve the metabolic processing of lipids within animals.

41 Claims, No Drawings

FOOD AND PHARMACEUTICAL COMPOSITIONS CONTAINING SHORT CHAIN MONOUNSATURATED FATTY ACIDS AND METHODS OF USING

FIELD OF THE INVENTION

The present invention pertains to food and pharmaceutical compositions which contain amounts of short chain monounsaturated fatty acids or their derivatives sufficient to increase the content of such fatty acids within the tissues of the organism to which the said compositions are administered.

BACKGROUND OF THE INVENTION

The chemical identity and quantity of fatty acids present in the diet of humans and other animals are known to have profound health consequences. Although popular attention to the harmful effects of dietary lipids has focused mainly on cholesterol, the biochemical properties of the fatty acids and their triglycerides have great significance in the development of degenerative conditions such as atherosclerosis and heart disease. A brief review of lipid uptake and processing is helpful in understanding the interconnections among dietary fatty acid composition, liver function, lipid metabolism and the development of atherosclerosis.

A. Biochemistry of Lipoproteins

The liver has a central role in the storage, synthesis, and metabolic transformations of lipids. One major function of the liver is to package triglycerides and cholesterol, which are insoluble in plasma, into particles called lipoproteins which can be carried in the bloodstream. The liver both secretes lipoproteins and also reabsorbs them after they have exchanged their lipid loads with peripheral tissues.

Four major classes of lipoproteins are known. All have an "oildrop" core of neutral lipid (triglyceride and/or cholesteryl esters) surrounded by an amphiphilic surface layer of phospholipids, cholesterol, and apolipoproteins. The larger the "oildrop" core, the less dense is the lipoprotein particle. In decreasing order of size, the four classes are:

1. Chylomicrons, which are secreted by the small intestine rather than the liver, and consist mostly of triglycerides absorbed from dietary fat;
2. very low density lipoproteins (VLDLs), which are secreted by the liver and contain mostly triglycerides;
3. low density lipoproteins (LDLs), which are generated in the liver from VLDL remnants, and contain mostly cholesteryl esters rather than triglycerides; and
4. high density lipoproteins (HDLs), which are secreted by the liver as phospholipid-rich discoidal particles, but which develop a lipid core by scavenging cholesterol from peripheral tissues.

1. Chylomicrons

Chylomicrons persist in plasma for only a brief time after a fatty meal. They are metabolized in the capillary beds of muscle and adipose tissue by the enzyme lipoprotein lipase (LpL) which is bound to the surface of the endothelial cells lining the capillaries. LpL hydrolyzes the triglyceride core of the chylomicrons, releasing free fatty acids. Some of the fatty acids immediately enter the adjacent muscle and adipose cells, while others are carried in the plasma bound to the circulating protein albumin. A large fraction (approximately one third) of the albumin-bound free fatty acids are taken up by the liver, about another third by skeletal muscles, and the remainder by other tissues, especially the myocardium. See Schiff, *Diseases of the Liver*, Ch. 22, "Fatty Liver," p. 824. In consequence, the fatty acids accumulated by heart, liver, and adipose tissue at least partially reflect the composition of dietary fats.

The chylomicron remnants left after lipolysis of the triglyceride core retain cholesteryl esters derived from dietary cholesterol. The chylomicron remnants are removed from the circulation by the liver, which thereby becomes a repository for dietarily derived cholesterol and esters thereof.

2. Very Low Density Lipoproteins

The liver cells, which have accumulated the fatty acids liberated from the diet by chylomicron lipolysis, resecrete these fatty acids in the form of triglycerides within VLDLs. Almost all the triglycerides found in the bloodstream more than a few hours after eating are present in VLDLs; hence a measurement of fasting plasma triglyceride concentrations is an indirect measurement of VLDL as well. As secreted by the liver, VLDLs are composed mostly of triglycerides. As is observed for chylomicrons, the triglycerides of VLDLs are lipolyzed by LpL, producing much smaller particles referred to as VLDL remnants. The intermediate density particles and VLDL remnants, produced by partial or extensive lipolysis of VLDLs, can accept cholesteryl esters from HDLs. Therefore over time these lipolyzed VLDLs become enriched in cholesterol. The liver removes some of the VLDL remnants from circulation, while others are converted by the liver into LDLs.

3. Low Density Lipoproteins and Atherosclerosis

The resulting LDLs differ from their VLDL precursors in two important respects: first, they are much smaller particles; and secondly, they contain almost exclusively cholesteryl esters rather than triglycerides. These differences make LDL the major source of the esterified cholesterol which is a prominent component of atherosclerotic plaques formed within the arterial walls. The LDL particles are small enough to pass between the endothelial cells lining the arteries and they thereby may penetrate into the arterial wall. LDLs appear to bind to the cells and connective tissues of the artery wall at specific susceptible sites. Frequently these bound LDL are engulfed by immune system scavenger cells called macrophages. Macrophages engorged with cholesteryl ester-laden LDL particles ("foam cells") constitute a key intermediate in atherosclerotic plaque formation. Although smooth muscle cells begin to proliferate around such a lesion site, and connective tissue is often elaborated within it, the cholesterol deposit with its associated foam cells forms the central core of the developing plaque.

In addition, atheromas may become calcified. The calcium deposits are in the form of "insoluble" calcium salts of fatty acids, similar to the soap scum which is produced by the reaction between "hard" ($Ca^{+2}$-rich) water and fatty acid anions. The fatty acid components are predominantly the high-melting, long chain saturated palmitate (C16:0) and stearate (C18:0). Polyunsaturated fatty acid components may be present as well. These are capable of undergoing cross-linking reactions to produce large, covalently bound complexes.

Atherosclerosis weakens the arterial wall and narrows the flow path of blood within the vessels. Atherosclerotic lesions frequently appear in particular in the coronary arteries, producing coronary heart disease. As the plaque increases in size, the coronary arteries may become completely blocked; when that occurs, the heart muscles are deprived of oxygen from the blood and the victim suffers a "heart attack", or myocardial infarction.

The risk of coronary heart disease increases dramatically as the plasma concentration of LDL cholesterol increases. Consequently, development of methods for lowering LDL cholesterol levels has become a major focus of medical research. The straightforward approach of reducing dietary cholesterol intake suffers from two limitations. The first is that cholesterol is present in all animal fats, and many Americans are unwilling to sacrifice their preferred diet. The second is that the liver and other tissues synthesize cholesterol de novo if the dietary supply is inadequate.

Cholesterol is an essential component of cellular membranes as well as a necessary precursor of metabolically important compounds such as bile acids and steroids. Cells obtain their necessary complement of cholesterol by taking up LDL particles through a specialized LDL receptor. The activity of the LDL receptors varies according to the cells, need for more cholesterol. Both peripheral cells and liver cells take up LDL through the receptor mechanism. However, unlike other cells, liver cells can both secrete and metabolically transform cholesterol, thereby removing it from the body. Thus when LDL receptor activity is low, the plasma LDL cholesterol level may be expected to rise, because LDL particles are not being removed from circulation as quickly as they are produced from VLDL remnants. This effect is accentuated by the fact that the liver removes VLDL remnants from circulation via the same LDL receptor; when LDL receptor activity is low, a smaller fraction of VLDL remnants is degraded, and consequently more remnants are converted into LDL particles instead. LDL receptor down-regulation thus decreases LDL clearance at the same time that the rate of LDL particle generation is increased. The result of this dual mechanism is that cholesterol levels climb markedly when LDL receptor activity decreases.

4. High Density Lipoproteins and Atherosclerosis

Whereas LDLs are a source of supply for cholesterol and have harmful atherogenic effects, HDLs scavenge excess cholesterol from peripheral tissues and protect against atherosclerosis. A high plasma HDL level is a negative risk factor for coronary heart disease, and is therefore considered highly beneficial. The liver secretes nascent HDL in the form of flat discoidal particles in which the major lipid class is phospholipids such as phosphatidylcholine. These phospholipids are composed of two fatty acid glyceryl esters, with a phosphate ester in the third position on the glycerol backbone. Excess cholesterol present in other cells is transferred to HDL. Over time an HDL particle develops a core of cholesteryl esters and assumes a more spherical shape. The accumulation of cholesteryl esters within HDL requires the assistance of the plasma enzyme lecithin: cholesterol acyl transferase (LCAT), which esterifies cholesterol scavenged from peripheral cells. HDLs eventually transfer their cholesteryl ester accumulation to intermediate density particles or VLDL remnants produced by lipolysis of VLDL. As indicated earlier, the cholesteryl ester enriched VLDL remnants are either taken up by liver cells or converted into LDLs. If taken up by liver cells, the VLDL cholesterol may be metabolically transformed into bile acids or secreted directly into bile. If incorporated into LDLs, this cholesterol will become available for reuse by peripheral cells. Thus the HDLs complete the cycling of cholesterol between liver and peripheral cells, and contribute to the elimination of cholesterol from the body via secretion into the bile.

Another possible benefit from HDL may be the removal of cholesterol from pre-existing atheromas, thereby shrinking or reversing atherosclerotic plaques. This effect has not been directly demonstrated, but indirect evidence of atheroma reversibility in the presence of elevated HDL levels supports this conclusion. In any case, elevated HDL levels have been shown clinically to protect against coronary heart disease and other atherosclerosis related diseases. See, e.g., Cotran, Kumar and Robbins, *Robbins Pathological Basis of Disease* (4th ed. 1989).

B. Lipid Metabolism and Pathology

As the preceding discussion indicates, the liver plays a central role in integrating dietary lipid consumption with circulating lipid levels and metabolic needs for lipid. Excessive dietary lipid and caloric intake can cause abnormal and possibly pre-pathological accumulation of triglyceride in the liver. The rate of liver triglyceride accumulation is affected by the plasma levels of insulin and glucose as well as of free fatty acid components; in turn, fatty acid utilization by the liver affects both glucose and insulin levels. Obesity, with its concomitant high rate of release of free fatty acids into the circulation, is a major predisposing factor in the development of insulin-resistant (type II or "adult-onset") diabetes. These relationships between high plasma fatty acid levels and fat accumulation in the liver, and between lipid utilization and incipient diabetes are highly relevant to the present discoveries.

Increased levels of free fatty acids in serum reflect active lipolysis, either within adipocytes to reduce peripheral fat deposits, or of plasma VLDL and chylomicrons by LpL. High dietary fat consumption naturally leads to an elevated rate of lipolysis of the chylomicrons generated from such dietary fat. Large amounts of triglyceride stored in adipose tissue also result in an enhanced rate of lipolysis within adipocytes. The released free fatty acids are used as a substitute for glucose as an energy source, especially by liver cells. Consequently serum glucose levels become elevated, since cells do not take up as much glucose. The pancreas then secretes more insulin in order to increase the rate of glucose uptake. After a prolonged period of exposure to excessive insulin secretion, cells develop the insulin resistance characteristic of type II diabetes. Circulating fatty acids thus provide a link between obesity, dietary fat, and the onset of insulin resistant diabetes.

When dietary fat consumption and/or adipose mass is high, the influx of free fatty acids into the liver exceeds its capacity to either metabolize these fats for energy or to secrete them as new VLDL. Consequently, triglycerides begin to accumulate in vesicles within the hepatocytes. The numerous intracellular triglyceride vesicles eventually may coalesce to produce fat globules visible by light microscopy. These large intracellular fat globules may produce hepatocyte injury or dysfunction and may even progress to macroscopically visible fatty streaks, a condition often referred to as "fatty liver." See Schiff, *Diseases of the Liver*, supra.

C. Dietary Lipid Structure and Pathology

Unsaturated fatty acids have a vinylic or carbon-carbon double bond at one or more positions along the acyl hydrocarbon chain. Hereinafter the structure of the fatty acids will be characterized by notations such as Cx:yn-a. Cx indicates that the fatty acyl group contains x carbon atoms; y indicates the number of carbon-carbon double bonds in the acyl chain; and n-a indicates that the most distal double bond terminates on the "a"th carbon counting from the terminal methyl end. The naturally occurring fatty acids are almost exclusively in the cis configuration, and all further references to unsaturated fatty acids will indicate the cis isomer unless explicitly stated otherwise.

One established approach to reducing plasma cholesterol levels is to consume a large proportion of dietary triglycerides as polyunsaturated fatty acid (PUFA) derivatives. The most widely occurring dietary PUFA is linoleic acid (C18:2n-6, or 9,12-octadecadienoic acid), which constitutes more than half of the fatty acid triglycerides of corn, soy, and safflower vegetable oils. The cholesterol lowering ability of PUFAs is believed to result from increased LDL receptor activity. See Spady & Dietschy, 82 Proc. Nat. Acad. Sci. USA 4576 (1985). This well established lowering of plasma LDL cholesterol concentration when PUFAs are substituted for dietary saturated fatty acids provides the rationale for the widespread substitution of a variety of vegetable oils for animal fats in cooking and food formulations. The American Heart Association in its Phase I and Phase II Recommended Diets has approved the use of PUFAs as part of a large scale dietary modification for the purpose of lowering cholesterol levels in the general population. See, e.g., S. M. Grundy, Disorders of Lipids and Lipoproteins, in *Internal Medicine*, Stein, ed. 2035,2046 (2nd ed. 1987).

However, PUFAs have significant deleterious health consequences as well as beneficial ones. Several negative effects of PUFAs may be ascribed to their increased rate of reaction via free-radical mechanisms. See, e.g., B. Halliwell and J. Gutteridge, "Lipid Peroxidation," Ch. 4 in *Free Radicals in Biology and Medicine*, (2d ed. 1989). PUFAs usually have two vinylic groups separated by a methylene carbon, as is exemplified by the 9,12 diene structure of linoleic acid. The bridging methylene carbon (e.g., C11 of linoleic acid) is activated towards free-radical substitution reactions by both of the adjacent vinylic groups. Consequently this methylene carbon reacts 10 to 20 times more readily in free radical reactions than does a methylene adjacent to only a single vinyl group. Their susceptibility to peroxidation and cross-linking reactions implicates PUFAs in several undesirable processes such as tissue aging and tumorigenesis. PUFAs have been implicated in increasing the incidence of human bowel cancer, in suppression of the immune system, in increasing the risk of cholesterol gallstones, and in promoting the oxidation of LDL trapped within the arterial wall.

Moreover, PUFAs lower the level of beneficial HDL cholesterol as well as the level of harmful LDL cholesterol. Since high HDL levels protect against atherosclerosis, the HDL-lowering effect of PUFAs could make them more rather than less atherogenic than saturated fatty acids.

Because of these drawbacks of PUFAs, some investigators have advocated the use of monounsaturated fatty acids (MUFAs). In particular, oleic acid (C18:1n-9) has been suggested as a nonatherogenic substitute for PUFAs. Oleic acid is a major component of olive oil, and some epidemiological evidence suggests that Mediterranean populations with high olive oil consumption have a reduced incidence of atherosclerosis and associated heart disease. Controlled human feeding studies, in which oleic acid was compared versus linoleic acid or saturated fats, reveal that oleic acid lowers serum LDL cholesterol about as well as does linoleic acid. However, unlike linoleic acid, oleic acid caused no reduction in HDL cholesterol levels. Based on this reported HDL sparing property of oleic acid, some researchers have urged that oleic acid should become a major source of dietary fat, whereas linoleic acid should be restricted to modest intakes. See S. M. Grundy, "Monounsaturated Fatty Acids and Cholesterol Metabolism: Implications for Dietary Recommendations," 119 J. Nutrition 529–533 (1989).

Medicinal properties also have been asserted for a particular type of C16:1 MUFA. Iwamura, et al. in U.S. Pat. No. 4,239,756 have disclosed the use of a compound which is a positional and geometric isomer of palmitoleic acid in a method for treating diabetes or improving lipid metabolism. The method involves oral or parenteral administration of alpha, betaunsaturated fatty acids of the structure $H_3C-(CH_2)_n-CH=CH-COOH$, where n=10, 12, 14, or 16. The fatty acids disclosed are therefore C14:1n-12, C16:1n-14, C18:1n-16, and C20:1n-18.

SUMMARY OF THE INVENTION

This invention encompasses compositions which are formulated to contain elevated levels of the MUFAs selected from the group composed of palmitoleic (hexadecenoic) acid (C16:1n-7) and its positional isomers C16:1n-6, C16:1n-5, C16:1n-4, and C16:1n-3, myristoleic (tetradecenoic) acid (C14:1n-5) and its positional isomers C14:1n-4 and C14:1n-3, and lauroleic (dodecenoic) acid (C12:1n-3), or their mixtures, whether as the free acids, salts, or esters thereof. Hereinafter, the above MUFAs are sometimes referred to as "short chain MUFAs" and the compositions in which they are contained are referred to as "DBD" compositions. The DBD compositions may comprise prepared foods, non-naturally occurring food components, food additives, or pharmaceuticals. The levels of short chain MUFAs in such compositions of matter are sufficiently high to produce beneficial improvements in the metabolic processing of lipids or glucose in animals to which these compositions of matter are regularly administered.

Beneficial improvements in the metabolic processing of lipids which are achieved by this invention are evidenced by different effects in various tissues. Generally, the metabolic processing of lipids may include any or all steps in the metabolic pathways: these include in part lipid uptake from dietary sources, hydrolysis, esterification of fatty acids to produce other lipid species, packaging of lipids into lipoproteins, lipid transport, lipid storage in tissues, lipid or lipoprotein cellular uptake, lipid synthesis, enzymatic modification and catabolism, and pathological lipid deposition in arteries, liver or other sites.

In the liver, the inventive compositions have been found to prevent or lessen fatty deposits. Such deposits occur in animals fed a high fat or high carbohydrate (which includes high alcohol) diet, and also in animals exposed to liver toxins such as halogenated hydrocarbons. In the experiments supporting the present invention, fatty deposits were evident upon microscopic examination of liver tissue from animals administered high fat olive oil or saturated fat dietary compositions, but surprisingly were absent in animals administered an equally high fat dietary composition containing elevated amounts of short chain MUFA triglycerides.

In the heart, the inventive compositions have been found to increase the level of palmitoleic acid or its esters, and unexpectedly to lower the level of saturated fatty acids or their esters within the heart tissue. As a previous study has demonstrated (63 Amer. J. Cardiology 269, 1989, see infra), increased palmitoleic acid and lowered saturated fatty acid levels correlate with a protective effect against ventricular arrythmias. Previous studies have not demonstrated how the said levels of palmitoleic and saturated fatty acids within heart tissue may be favorably manipulated, however. The present invention achieves both improvements by administering a composition containing elevated amounts of short chain MUFA triglycerides.

In the blood, the inventive compositions have been found to lower the plasma LDL concentration, compared to the plasma LDL concentration obtained when the short chain MUFAs are replaced in the diet either with saturated fatty acids or with unsaturated fatty acids which are not short chain MUFAs. The inventive compositions also elevate the concentration of plasma HDL compared to the plasma HDL concentration obtained when the short chain MUFAs are replaced in the diet with saturated fatty acids. Lowering the level of plasma LDL and increasing the level of HDL within the circulation, and increasing the HDL/LDL ratio are beneficial in preventing atherosclerosis and coronary heart disease.

In adipose tissue, the inventive compositions have been found to lower the triglyceride content per unit weight of adipose tissue. This necessarily means that other tissue components, such as proteins, carbohydrates, nucleic acids and cellular water which are associated with cellular metabolic functions, are increased; and that the proportion of each adipocyte which is occupied by triglyceride is lowered. The decreased intracellular triglyceride deposits indicate that triglyceride is hydrolyzed more readily from adipose tissue when animals are administered a dietary composition containing elevated amounts of short chain MUFA triglycerides.

Beneficial improvements in the metabolic processing of glucose are achieved by this invention by lowering serum glucose concentrations which are abnormally elevated in insulin-resistant animals. Insulin-resistant elevated glucose concentrations occur in animals which are obese and have an excessive caloric intake. In humans, this condition is known as type II diabetes. In the experiments supporting the present invention, we have demonstrated that serum glucose levels can be normalized even in obese animals having excessive caloric intake, by administering a dietary composition containing elevated amounts of short chain MUFA triglycerides.

The compositions of the present invention are "formulated" in the sense that the fatty acid content of the food or pharmaceutical composition is manipulated or adjusted to provide a sufficient amount of the short chain MUFAs. A "sufficient amount" of the short chain MUFAs in any given composition is determined in relation to the total amount of the said short chain MUFAs required for regular administration in order to produce the particularly desired beneficial improvement.

This invention contemplates that the said formulated compositions should be regularly or systematically administered in order to produce beneficial improvement. The stated short chain MUFAs are incorporated into the structural lipids of the animal to which they are administered. If the short chain MUFAs are administered in low amounts or at long intervals, they will not become a significant proportion of the fatty acids present in these structural lipids. In consequence the beneficial improvements cannot be achieved.

DETAILED DESCRIPTION OF THE INVENTION

A. Theory of the Invention

While we do not wish to be bound by theory, we believe that a brief presentation of the hypotheses which led us to perform these investigations will be helpful in understanding the empirical results which we have obtained.

We have hypothesized that the melting characteristics of fatty acids and their derivatives are crucial in determining whether they will be atherogenic or nonatherogenic. Solid-to-fluid phase transition temperatures are an indicator of the viscosity properties of the fatty acyl chains. The atherogenic saturated fats, such as palmitic (C16:0) and stearic (C18:0) triglycerides, are solids at both room (about 25° C.) and physiological (about 37° C.) temperatures. Triglycerides having the same length acyl chains but with one or more unsaturated (vinylic) bonds are liquids at such temperatures. Naturally occurring triglycerides are mixtures of various lipid species and contain esters of several fatty acids which may differ in both acyl chain length and degree of saturation. The relative proportions of high and low melting fatty acyl groups determine the melting behavior of the mixture. For example, lard (from pigs), tallow (from cattle) and mutton tallow (from sheep) are solid fats at room temperature, and between 40 and 50% of their acyl groups are saturated C16:0 and C18:0 The MUFA oleic acid (C18:1) constitutes about 40 to 50% of their acyl content and much of the reminder is the PUFA linoleic acid (C18:2). By contrast, most vegetable oils, which are liquids at room temperature, have only 10-20% of palmitic and stearic acid esters, with the reminder mostly unsaturated oleic and linoleic acid esters. The lower atherogenicity of these vegetable oils thus roughly correlates with their low melting temperatures. Unfortunately, whereas polyunsaturation permits vegetable oils to achieve greater fluidity, lower melting temperatures, and lower atherogenicity, it also makes them susceptible to undesirable crosslinking and peroxidation reactions causing the formation of insidious polymers.

The rank order of melting temperatures of triglycerides in general is reflected in the melting temperatures of the corresponding phospholipids, free fatty acids and acid salts derived from them. The melting temperature of the free fatty acids liberated from a triglyceride source by hydrolysis is frequently used to characterize the triglyceride and is known as the "titer." Titer decreases as the fatty acid structure goes from saturated to unsaturated, and also as the acyl chain length becomes shorter. The position of the vinylic bond is also an important determinant of the melting temperature of unsaturated fatty acids: titer decreases as the position of the double bond moves away from the carboxyl end of the molecule.

Similarly, the melting behavior of phospholipids reflects the melting trends of their constituent fatty acids. For example, the solid to fluid phase transition temperature of the physiologically important phospholipid dipalmitoylphosphatidylcholine (DPPC) is about 41.5° C., meaning that bilayer membranes made solely from DPPC are in the solid phase at physiological temperature. When the central acyl group is replaced with oleic acid (C18:1) to make palmitoyloleoylphosphatidylcholine (POPC), the phase transition temperature is lowered to near 0° C., meaning that a POPC membrane is very fluid at 37° C. Thus incorporation of an unsaturated fatty acid into a phospholipid produces a dramatic lowering of the rheological characteristics of the resulting membrane bilayers.

Although scientifically based claims of health benefits derived from dietary MUFAs previously have been asserted only for oleic acid, other monounsaturated fatty acids also occur naturally. The commonest are 11-eicosenoic acid (C20:1n-9) and 13-docosenoic acid (C22:1n-9), both of which are found in high levels in some oilseed plants such as jojoba and rapeseed. The shorter chain MUFA 9-palmitoleic acid (C16:1n-7 occurs as a minor component (ca. 2%) in olive and cottonseed oils and in trace amounts in a few other commercially available vegetable oils. Palmitoleic acid occurs in somewhat higher amounts in animal fat triglycerides such as lard and tallow (up to 5%) and in still higher levels in some fish oils such as sardine oil. The next lower homologue, myristoleic (9-tetradecenoic) acid (C14:1n-5), occurs in minor amounts in animal fat and in butter. The even lower homologue, lauroleic (9-dodecenoic) acid (C12:1n-3), occurs rarely and in small amounts in natural sources.

Although the short chain MUFAs palmitoleic, tetradecenoic and dodecenoic acids have been known for many years, they have not been suggested as useful compounds for dietary modification. The advocates of oleic acid as a dietary replacement for PUFAs and saturated fats have not provided similar teachings for the utility of the shorter chain homologues such as palmitoleic acid. Little or no significance has been attributed by the medical or biochemical community to the presence of palmitoleic and myristoleic acids as important constituents of animal lipids.

One recent study did observe an unexpected negative correlation between palmitoleic acid concentrations in the adipose tissue of patients who had suffered a recent myocardial infarction and their incidence of subsequent serious cardiac ventricular arrhythmias. Abraham, Riemersma, Wood, Efton and Oliver, "Adipose Fatty Acid Composition and the Risk of Serious Ventricular Arrhythmias in Acute Myocardial Infarction," 63 Amer. J. Cardiology 269 (1989). These investigators had hypothesized that high tissue levels of PUFAs, and in particular linoleic acid, would protect heart attack victims from developing life-threatening arrhythmias in their damaged hearts. Previous studies had shown that adipose tissue fatty acid composition is similar to that of heart muscle, and the investigators therefore analyzed the fatty acid composition of biopsied adipose tissue from myocardial infarct patients as an indicator of the lipid composition of their heart muscle. These investigators did not find the predicted correlation between tissue linoleic acid levels and protection against subsequent arrythmias. However, they did observe that the patients who did not develop arrythmias had significantly lower levels of saturated fatty acids and significantly higher levels of palmitoleic acid, compared with the arrythmic group. The authors suggested that "saturated fatty acids in cardiac membranes may lead to greater vulnerability to ventricular arrhythmias," but did not draw the corresponding inference that palmitoleic acid in cardiac membranes may be protective.

Based on our hypothesis concerning the beneficial role of lower melting and more fluid fatty acids, we believe that the correlation between high palmitoleic acid levels and protection against arrythmias is but one example of the general health benefits conferred by short chain MUFAs. The investigators who published the correlation failed to appreciate that short chain MUFAs may be beneficial, apparently because the scientific literature does not teach this. Their failure to assert that high palmitoleic acid levels might be the cause of the observed cardiac protection is therefore quite comprehensible in view of the prevailing scientific neglect of short chain MUFAs.

Our hypothesis, that the beneficial effects of dietary PUFAs and MUFAs on health may be characterized by and understood in terms of the lower melting temperatures, lower viscosities, and greater fluidity of the lipids which incorporate such fatty acids, has led us to postulate that the heretofore overlooked short chain MUFAs may confer health benefits comparable to or greater than those already demonstrated for oleic acid (C18:1). As used herein, the term "short chain MUFAs" refers to monounsaturated fatty acids which are shorter than oleic acid (C18:1n-9), which is well known to provide health benefits. In particular, we have postulated that the short chain MUFAs palmitoleic (hexadecenoic) acid C16:1n-7), myristoleic (tetradecenoic) acid (C14:1n-5), and lauroleic (dodecenoic) acid (C12:1n-3), and lipids incorporating them may be beneficial to health when administered as foods or pharmaceuticals. These C16:1n-7, C14:1n-5, and C12:1n-3 acids and their esters are even lower melting and less viscous than oleic acid due to their shorter chain length and favorably positioned unsaturated bonds. Moreover, we propose that positional isomers of these short chain MUFAs in which the vinylic bond is located even farther away from the carboxyl group will have similar or possibly greater utility. This postulate follows from the fact that monounsaturated fatty acid lipids melt at lower temperatures as the double bond is positioned more remotely from the carboxyl group. Thus C16:1n-6, C16:1n-5, C16:1n-4, C16:1n-3, C14:1n-4, and C14:1n-3 are all predicted by our postulate to confer health benefits. In addition, all of the aforementioned C16:1, C14:1 and C12:1 fatty acids share with oleic acid the highly beneficial greater stability of monounsaturated compared to polyunsaturated alkyl structures.

The greater fluidity of the above short chain MUFAs may be expected to be advantageous in several ways. For one, the lipases which hydrolyze triglycerides to yield free fatty acids are known to require fluid rather than solid triglycerides as substrates. The greater fluidity of the short chain MUFAs and their triglycerides may permit lipoprotein lipase to hydrolyze chylomicrons and VLDL more efficiently when they are enriched in C16:1, C14:1, and C12:1. This might directly lower VLDL levels and ultimately lower LDL cholesterol levels. In addition, fatty acids might be released more readily from adipose tissue due to the enhanced activity of lipases on highly fluid C16:1, C14:1 and C12:1 triglycerides, thereby helping to reduce these fat deposits.

The rate of formation of cholesteryl esters by the enzyme LCAT is known to increase when the fatty acid being esterified is more fluid. See Emken, Biochemistry of Unsaturated Fatty Acid Isomers, 60 J. Amer. Oil Chem. Soc. 995, 1001 (1983) (cis-C18:1n-9 is esterified more rapidly than the higher melting trans-C18:1n-9, cis-C18:1n-6, and cis-C18:1n-5 isomers). This esterification step is rate-limiting in the transfer of cholesterol from peripheral cells to HDL and thence to VLDL remnants. Therefore high LCAT activity is important to the HDL-mediated removal of cholesterol from peripheral tissue. The even lower melting C16:1, C14:1, and C12:1 fatty acids may be expected in light of this invention to promote this activity and therefore contribute to the protective effect of HDL. The HDL cholesterol concentration in plasma therefore is also expected to increase due to administration of these short chain MUFAs.

Triglyceride contained within intracellular vesicles might also be processed and transported more readily when lower viscosity C16:1, C14:1, and C12:1 MUFAs comprise a significant fraction of the lipids. This might affect the rate of VLDL formation within liver cells, and therefore lessen fatty accumulation and deposits within the liver.

Membranes containing elevated proportions of C16:1, C14:1, and C12:1 phospholipids would be more fluid than normal membranes composed of more saturated and longer acyl chain fatty acid esters. This might necessitate greater use of cholesterol by cells, since one functional role of cholesterol when incorporated into phospholipid bilayers is to rigidify excessively fluid membranes. Increased cellular uptake of LDL to satisfy the cells, enhanced cholesterol requirement in membrane formation would be expected to lower LDL cholesterol levels in light of the teachings herein.

The C16:1n-(7, 6, 5, 4, or 3) and C14:1n-(5, 4, or 3) compounds of the present invention also are very different from the alpha, beta-unsaturated fatty acids, C16:1n-14 and C14:1n-12, disclosed by the Iwamura patent. The alpha, beta-unsaturated fatty acids have chemical properties significantly different from those of the monounsaturated fatty acids of the present invention, because the double bond in the former compounds is conjugated with the carbonyl group. This double bond is therefore highly reactive toward both electrophilic and nucleophilic addition reactions, in contrast to the relatively much more stable isolated double bond of the compounds disclosed herein. The alpha, beta-unsaturated fatty acids are in fact transiently occurring intermediates in biological oxidative degradation of fatty acids via the "beta-oxidation" pathway. Thus upon administration they probably would be preferentially metabolized rather than incorporated into tissue. Also, the Iwamura patent does not specify the geometry of the double bond. However, the claimed compounds are isolated from mollusks. The naturally occurring alpha,-beta-unsaturated fatty acids produced by the beta-oxidation pathway are trans rather than cis, suggesting that the Iwamura compounds are trans. The fatty acids isolated by Iwamura are also stated to be identical with synthetically produced material; consistent with this interpretation, the alpha, beta-unsaturated fatty acids produced by the usual organic syntheses are predominantly in the transconfiguration. By contrast, the MUFAs which are the subject matter of the present invention are in the cis configuration. Finally, alpha, beta-unsaturated fatty acids are high melting compounds both as free acids and as esters. This contrasts with the low melting properties of the unconjugated cis-MUFAs of this invention, in which at least seven saturated carbons intervene between the carbonyl and the cis-double bond. We have found that this marked difference in physical properties has great physiological significance, as the preceding discussion of the role of low melting fatty acids would indicate. The Iwamura patent also does not disclose a preferential benefit from the shorter chain C14:1n-12 and C16:1n-14 compounds in comparison with the longer chain C18:1n-16 and C20:1n-18 members of the series. By contrast, the present invention is directed exclusively to the lower melting short chain MUFAs.

B. Experimental

Based on these anticipated benefits, we undertook feeding experiments to demonstrate that animals incorporate high dietary levels of the short chain MUFA palmitoleic acid into their tissue lipids. The lipids of liver, plasma, heart and adipose tissue from rats fed diets enriched in palmitoleic acid triglycerides were analyzed to provide evidence that these tissue contain elevated levels of palmitoleic acid, compared to tissues from rats fed control diets. Standard clinical chemistry tests were performed to indicate the metabolic state of the rats fed the palmitoleic acid enriched versus the control diets. Finally, histologic analyses of liver tissues from control and palmitoleate fed rats were performed to assess the health of this central lipid processing organ.

1. Preparation of a Formulated Composition Containing Short Chain MUFAs

Although the present invention encompasses pharmaceutical compositions as well as dietary compositions for animal experiments, we chose to formulate a prepared food containing elevated amounts of the short chain MUFA palmitoleic acid (C16:1n-7). A feeding study has an advantage compared to a study requiring administration of a pharmaceutical, in that the experimental animals will self-administer the food composition. We chose to limit the study to the single short chain MUFA palmitoleic acid, rather than including groups fed the congeneric myristoleic (tetradecenoic) (C14:1n-5) and lauroleic (dodecenoic) (C12:1n-3) acids, to increase the likelihood of obtaining significant results while using a minimal number of experimental animals.

As the preceding discussion of theory indicates, a beneficial effect on lipid metabolism should be expressed when the proportion of short chain MUFAs incorporated into tissue lipids becomes large enough to affect the physiochemical properties, such as fluidity and melting temperature, of the tissue lipids. Therefore both the total amount of short chain MUFAs and their relative proportion in the diet are expected to be significant. In the present case, palmitoleic acid constituted 21.8 mol % of the fatty acids present in the prepared food given to the experimental group of rats.

This molar percentage of palmitoleic acid is quite high compared to the amounts present in most natural fats and oils: 13% for sardine oil, 5% for tallow, 3% for lard, 5% for butter, 0.5–2% for cottonseed and olive oils, and only trace amounts in almost all other commercially significant vegetable oils. See "Composition and Constants of Natural Fats and Oils" (Sherex).

The proportion of fat in the formulated diet was also relatively high: 48.4% of total calories came from fat.

This is slightly higher than but comparable to the fat content of the typical American diet, which derives 40–45% of its calories from fat. See Guyton, Textbook of Medical Physiology (4th ed. 1971) at 802. Some representative foods and their percent calories from fat are listed in Table I (calculated from data in J. Weihrauch, "Provisional Table of the Fatty Acid and Cholesterol Content of Selected Foods," USDA Human Nutrition Information Services, 1984) Clearly a number of common dietary items contain about 48% or more of their calories as fat. Thus the diet administered to rats in the study is not so laden with fat that it is outside the range of what a great many Americans normally consume.

TABLE I

| Food Items | % Calories From Fat |
|---|---|
| Peanut Butter | 77% |
| Ground Beef, cooked-well done | 58% |
| Bacon, fried crisp | 77% |
| Chicken, dark meat, fried | 54% |
| Frankfurter, beef | 83% |
| Potatoes, french-fried | 47% |
| Pound Cake | 55% |
| Veal Cutlet | 46% |
| Doughnut, yeast | 58% |
| Egg, hard boiled | 65% |
| Cheese, cheddar | 73% |
| Milk, whole (3.3% fat) | 48% |

The high fat levels of this experimental diet were formulated to insure that the experimental animals consumed a large quantity of palmitoleic acid. Naturally, in a prepared food formulated for nonexperimental purposes, and especially for human consumption, the proportion of total fat and also the molar percentage of palmitoleic acid may be considerably lower, consistent with this invention.

Macadamia nuts were chosen as a raw material from which to isolate palmitoleic acid triglycerides for this formulated dietary composition. Unlike any other commercial crop, macadamia nuts contain high levels of palmitoleic acid, which comprises in excess of 19% of the fatty acid composition of macadamia nut oil. In addition, the other fatty acids of macadamia nut oil are closely similar in both identity and quantity to those present in olive oil. This similarity was extremely fortuitous for implementing the rat feeding experiments, because olive oil provided an ideal positive control. Olive oil contains oleic acid as its major component and is already established as a beneficial dietary fat source. By comparing the palmitoleic acid enriched diet (hereinafter designated POL) against an oleic acid enriched diet (hereinafter designated OLO), we could conclude that any equivalent or superior beneficial effects on lipid metabolism indicate clear utility for palmitoleic acid.

As Table II indicates, the minor fatty acid components of OLO were quantitatively similar to those of POL. Moreover, the two provided similar total amounts of saturated FAs (12:0+14:0+16:0+18:0), of MUFAs (16:1+18:1) and of total combined unsaturated fatty acids (16:1+18:1+18:2+20:4). The striking difference between the olive oil and macadamia nut oil compositions was that the latter contained a much larger fraction of MUFA which was 16:1 rather than 18:1.

TABLE II

| Fatty Acid Composition (mol %) Of POL, OLO and HF Diets | | | |
|---|---|---|---|
| Fatty Acid | POL | OLO | HF |
| 12:0 | 0.24 | 0.00 | 57.83 |
| 14:0 | 1.02 | 0.00 | 17.38 |
| 16:0 | 11.58 | 12.40 | 8.08 |
| 18:0 | 2.33 | 2.33 | 6.19 |
| 16:1 | 21.76 | 0.74 | 0.00 |
| 18:1 (cis) | 43.47 | 60.67 | 2.91 |
| 18:1 (trans) | 2.81 | 2.04 | 0.00 |
| 18:2 | 15.42 | 21.83 | 7.61 |
| 20:4 | 1.38 | 0.00 | 0.00 |
| cis-MUFAs | 65.23 | 61.41 | 2.91 |
| Total unsaturated FA | 84.84 | 85.28 | 10.52 |
| Total saturated FA | 15.17 | 14.73 | 89.48 |

Although macadamia nuts have been suggested as an oilseed crop (see Macfarlane and Harris, "Macadamia Nuts as an Edible Oil Source", Amer. Oil Chem. Soc. Monograph 1981, 103–108), we were unable to locate a commercial source of the oil. Consequently, we extracted the oil from ground macadamia nuts by solvent extraction with hexane, followed by solvent evaporation under reduced pressure.

Olive oil for formulating the oleic acid enriched comparative dietary composition was obtained from commercial sources. A second comparative dietary composition containing only saturated fatty acids was also developed. Coconut oil was completely hydrogenated to provide a totally saturated fat source. This was substituted for the macadamia nut or olive oils in the formulation recipe. The resulting formulated dietary composition differed substantially from the two other compositions in its quantitative fatty acid content as Table II clearly indicates. Fully three-fourths of the fatty acids present in the hydrogenated fat composition (hereinafter designated HF) are the short chain saturated lauric (dodecanoic) (C12:0) and myristic (tetradecanoic) (C14:0) acids. No MUFAs or PUFAs remained in the hydrogenated coconut oil; the small amounts present in the final HF composition were derived from added corn oil. This unusual fatty acid profile was chosen because the resulting triglycerides, even though they are fully saturated, are quite low melting due to the shortness of the acyl chains. Thus some beneficial effects on lipid metabolism may be produced by the HF diet despite its high saturation, as a consequence of the low melting short acyl chains. However, we anticipated that beneficial effects would not be as widespread or as pronounced as with the POL and OLO diets, in part because C12:0 and C14:0 are known to be subject to chain elongation reactions which can convert them to the higher melting and atherogenic C16:0 and C18:0 fatty acids.

In formulating the dietary compositions for rat feeding studies, we combined 200 g of macadamia nut oil, olive oil, or hydrogenated coconut oil with 50 g of corn oil. The corn oil served as a source of the essential fatty acid linoleic acid (C18:2), which is present in low amounts in macadamia nut oil and olive oil. This oil mixture was blended with 250 g of casein protein, 224.9 g sucrose, 15 g maltodextrin, 62.5 g of cellulose fiber, 56.3 g of mineral and vitamin mix, 3.8 g of methionine, 2.5 g of choline bitartrate, and 0.05 g of ethoxyquin antioxidant. The remaining dietary components are standard in the AIN-76 diet widely used for rat maintenance feeding. The POL, OLO, and HF diets each contained 21.75% protein, 25.25% fat, and 38.63% carbohydrate, and provided 4.69kcal/g energy. As previously indicated, 48.4% of total calories in these diets came from fat, a high value but only slightly greater than the American dietary norm. Just under two-thirds of the fatty acids present in the macadamia and olive oil diets were monounsaturated (either C16:1n-7 or C18:1n-9).

2. Animal Feeding Study

The formulated dietary compositions described above were fed to three groups of 6 rats each for a period of 8 weeks. These formulated diets constituted the only food allowed the animals during this period. The rats were housed individually in wire-bottom cages. Food and water were available ad libitum.

Male Sprague-Dawley rats 4–5 weeks old and weighing initially about 105 g were used for all three groups. The animals were weighed weekly. Their food intake was recorded three days per week.

After 8 weeks of feeding, the rats were sacrificed by decapitation. Blood was collected, heparinized, and centrifuged to harvest plasma, which was used for a variety of clinical tests. Liver, heart, and epididymal fat pads were examined in situ. removed, rinsed, and stored at −70° C. until fatty acid analysis could be performed. A portion of fresh liver tissue was fixed for morphological examination to determine the general health of the organ and the extent of fatty deposition.

Fatty acid analyses were performed on samples of liver, fat pad, heart and plasma taken from each rat. The tissue samples were weighed and extracted using the Folch procedure (acidified chloroform/methanol). The organic layer was evaporated and the residue saponified in ethanolic KOH. Methyl derivatives of the fatty acids were formed. These were identified and quantitated by capillary gas chromatography using a flame ionization detector. Similar analyses were also performed on the formulated dietary compositions and the source oils.

Plasma samples were further analyzed using standard clinical chemistry tests for triglycerides and total cholesterol, as rough indicators of VLDL and LDL levels; for plasma glucose as an indicator of diabetic or prediabetic conditions which might arise because of obesity and elevated plasma fatty acid levels; for uric acid, a degradation product of purine metabolism which is excreted in urine; for creatinine and blood urea nitrogen, terminal metabolites of proteins which are secreted continuously in urine and indicate renal function; for bilirubin, a breakdown product of hemoglobin which is removed from the blood by the liver, and which becomes elevated when liver function is impaired; for calcium ion, a regulator of membrane permeability and muscle contractility; for glutamate-pyruvate and glutamate-oxaloacetate transaminases, enzymes required for protein metabolism by liver cells and which are elevated in plasma when liver cell breakdown occurs; for alkaline phosphatase, an enzyme present in liver cells which is also elevated in plasma secondary to liver cell injury; for amylase, a carbohydrate digesting enzyme secreted by the pancreas and elevated in the blood when pancreatic cells are damaged; and for total protein, albumin, and albumin-to-globulin ratio, which are measures of protein secretion by the liver.

All feeding, tissue examination, and chemical analysis procedures were performed under double blind conditions. At the conclusion of the experiments the identities of the three groups of rats were revealed to be as follows:
Group I—POL diet
Group II—HF diet
Group III—OLO diet 3. Results The three groups were remarkably similar in the total weight of food consumed, the total body weight gain, and the ratio of weight gain to weight of food consumed (Table III).

TABLE III

Mean Food Consumption and Weight Gain of Rats (data in grams)

| Group | Day 0 | Day 62 | Weight Gain | Weight of Food Consumed | Ratio % |
|---|---|---|---|---|---|
| POL | 105 | 490 | 385 | 1018 | 37.7 |
| HF | 105 | 476 | 371 | 1099 | 34.0 |
| OLO | 104 | 497 | 393 | 1105 | 35.5 |

The average weight gain among the three groups differed by only 6%, while the weight of food consumed differed by about 7.9% between the height and lowest groups. The percent ratio of weight gained to weight of food consumed is a rough indicator of the efficiency of utilization of the diet, and ranges from 34.0% for the HF group to 37.7% for the POL group. The differences in weight gain among the three groups are insignificant, but the efficiency of utilization is slightly higher in the POL group than in the other two. Thus palmitoleic acid appears to be at least as nutritive as the fatty acids present in the two comparison groups in the study, and may be somewhat better absorbed.

The weight percent composition of fatty acids isolated from epididymal fat pad adipose tissue, liver, heart, and plasma are given in Table IV, along with the composition of the dietary fats for comparison.

TABLE IV

Mean Fatty Acid Content of Rat Tissues And Corresponding Diet (% by weight)

| Fatty Acid | Diet | Fat Pad | Liver | Heart | Plasma (w/v) |
|---|---|---|---|---|---|
| POL Group | | | | | |
| C12:0 | 0.2 | 0.0 | 0.0 | 0.6 | 0.6 |
| C14:0 | 1.0 | 1.0 | 0.8 | 0.7 | 0.7 |
| C16:0 | 11.6 | 13.0 | 26.0 | 15.0 | 18.6 |
| C18:0 | 2.3 | 1.6 | 8.3 | 24.0 | 9.6 |
| C16:1 | 21.8 | 17.3 | 7.7 | 2.9 | 8.7 |
| C18:1 | 46.3 | 51.5 | 42.7 | 19.9 | 36.6 |
| C18:2 | 15.4 | 15.3 | 6.0 | 15.6 | 10.6 |
| C20:4 | 1.4 | 0.4 | 8.4 | 21.6 | 14.6 |
| HF Group | | | | | |
| C12:0 | 57.8 | 40.4 | 1.7 | 2.2 | 14.5 |
| C14:0 | 17.4 | 14.5 | 5.6 | 3.1 | 8.6 |
| C16:0 | 8.1 | 12.9 | 32.0 | 16.9 | 21.2 |
| C18:0 | 6.2 | 2.8 | 13.8 | 26.9 | 13.1 |
| C16:1 | 0.0 | 3.0 | 3.7 | 0.7 | 2.4 |
| C18:1 | 2.9 | 13.0 | 19.4 | 8.4 | 12.4 |
| C18:2 | 7.6 | 13.3 | 14.0 | 25.2 | 16.1 |
| C20:4 | 0.0 | 0.0 | 9.9 | 16.6 | 11.8 |
| OLO Group | | | | | |
| C12:0 | 0.0 | 0.0 | 0.0 | 0.3 | 0.4 |
| C14:0 | 0.0 | 0.7 | 0.7 | 0.5 | 0.6 |
| C16:0 | 12.4 | 14.5 | 27.7 | 16.9 | 21.2 |
| C18:0 | 2.3 | 1.5 | 8.8 | 25.6 | 9.6 |
| C16:1 | 0.7 | 2.2 | 1.9 | 0.5 | 1.9 |
| C18:1 | 62.7 | 61.6 | 45.3 | 19.3 | 42.3 |
| C18:2 | 21.8 | 19.5 | 7.4 | 15.5 | 11.4 |
| C20:4 | 0.0 | 0.0 | 8.1 | 21.4 | 12.8 |

Several interesting features may be discerned from these data. First, the animals in all three dietary groups either synthesized or selectively concentrated C16:0 and C18:0, presumably in their livers, and incorporated those saturated fatty acids into the liver, heart and plasma in proportions higher than those of the diets. The POL diet animals incorporated lower proportions of C16:0 into these three tissues than did animals in the other diet groups, although the POL diet is intermediate in C16:0 content. The POL animals also incorporated less C18:0 into heart tissue than did the other groups, although the levels of C18:0 in liver and plasma were equal in the POL and OLO diet groups. The HF diet contained high levels of C14:0, which was nearly absent in the other two diets. The HF group animals incorporated C14:0 into all tissues at levels lower than those in the diet, with the lowest level obtained in the heart at 3.1%. The POL and OLO animals incorporated C14:0 into all tissues at levels of 1% or less. A similar pattern occurred with C12:0. These shorter chain saturated fatty acids did not accumulate in those tissues, perhaps because they were preferentially metabolized for energy or were converted into longer chain fatty acids.

The concentrations of fatty acids per gram of tissue for animals from the three dietary groups are given in Table V.

TABLE V

Concentrations of Fatty Acids in Rat Tissues (ug/g)

| Fatty Acid | Fat Pad | Heart | Liver | Plasma (w/v) |
|---|---|---|---|---|
| POL Group | | | | |
| C12:0 | 0.0 | 59.6 | 0.0 | 16.8 |
| C14:0 | 7.2 | 69.8 | 356.4 | 20.0 |
| C16:0 | 90.4 | 1615.7 | 11040.8 | 542.6 |
| C18:0 | 10.9 | 2580.7 | 3537.8 | 280.5 |
| C16:1 | 120.3 | 313.5 | 3261.5 | 259.1 |
| C18:1 | 359.0 | 2142.9 | 18119.3 | 1068.9 |
| C18:2 | 106.2 | 1687.6 | 2558.7 | 308.5 |
| C20:4 | 2.9 | 2329.9 | 3566.5 | 426.9 |
| Total | 696.8 | 10799.6 | 42441.0 | 2918.3 |
| Saturated | 108.5 | 4325.8 | 14935.0 | 859.9 |
| Monounsaturated | 479.3 | 2456.4 | 21380.8 | 1323.0 |
| HF Group | | | | |
| C12:0 | 384.1 | 254.6 | 563.8 | 488.1 |
| C14:0 | 138.2 | 359.6 | 1847.9 | 291.4 |
| C16:0 | 123.0 | 1965.3 | 10624.2 | 717.4 |
| C18:0 | 26.3 | 3129.4 | 4577.4 | 441.1 |
| C16:1 | 28.0 | 77.4 | 1224.0 | 81.3 |
| C18:1 | 123.8 | 974.0 | 6457.3 | 418.8 |
| C18:2 | 126.9 | 2930.4 | 4657.8 | 543.5 |
| C20:4 | 0.4 | 1932.8 | 3285.3 | 396.9 |
| Total | 951.0 | 11623.4 | 33237.7 | 3378.4 |
| Saturated | 671.9 | 5708.9 | 17613.3 | 1938.0 |
| Monounsaturated | 151.8 | 1051.4 | 7681.3 | 500.1 |
| OL Group | | | | |
| C12:0 | 0.0 | 35.9 | 0.0 | 14.9 |
| C14:0 | 4.0 | 57.9 | 318.1 | 20.0 |
| C16:0 | 95.8 | 1871.2 | 11838.4 | 755.7 |
| C18:0 | 10.0 | 2834.3 | 3774.6 | 341.5 |
| C16:1 | 14.7 | 50.7 | 808.8 | 66.6 |
| C18:1 | 408.2 | 2136.2 | 19351.0 | 1510.1 |
| C18:2 | 128.9 | 1718.8 | 3153.5 | 406.4 |
| C20:4 | 0.0 | 2372.4 | 3452.2 | 457.3 |
| Total | 662.1 | 11077.3 | 42696.5 | 3572.4 |
| Saturated | 109.8 | 4799.3 | 15931.1 | 1132.1 |
| Monounsaturated | 422.9 | 2186.9 | 20159.8 | 1576.7 |

One unanticipated beneficial effect which is apparent from this pattern of fatty acid distribution is that the POL group animals have lower total levels of saturated fatty acids in their heart tissue (4.33 mg/g) than do either the OLO (4.80 mg/g) or HF (5.7 mg/g) groups. While this effect is only mildly surprising when the POL group is compared to the highly saturated HF group, it is quite surprising when POL is compared to the OLO group. Apparently heart tissue adjusts the relative concentrations of various fatty acids in a highly selective manner, perhaps to maintain a preferential level of membrane fluidity. Thus although the POL diet actually contained slightly greater total levels of saturated fatty acids than did the OLO diet, the resulting POL heart tissue unexpectedly contained lower total levels of saturated fatty acids. The magnitude of this lowering apparently is sufficient to confer cardiac protection. In the report published in *Amer. J. Cardiology*, supra, the arrhythmia-free group had 4.4% lower total saturated fatty acid content than the arrhythmic group. In our feeding study, the hearts of POL group rats contained total saturated fatty acids 9.8% lower than the OLO group and 24.2% lower than the HF group (saturated fatty acid).

The increase in palmitoleic acid levels in all tissues, including heart, due to the administration of palmitoleic acid enriched triglycerides is dramatic. These values are included in Tables IV and V. The fractional C16:1 content of heart tissue from POL rats (2.9%) increased nearly 600% compared to OLO rats (0.5%) and more than 400% compared to HF rats (0.7%). By comparison, in the *Amer. J. Cardiology* study the increase in C16:1 content in nonarrythmic patients compared to arrythmic patients was only about 11%. Therefore the observed increase in C16:1 content due to the POL diet is clearly of a magnitude sufficient to produce beneficial effects on the heart.

In all tissues examined, including liver, plasma, and adipose tissue as well as heart, the content of C16:1n-7 was much greater for animals fed the POL diet than in those fed either the OLO or HF diets. However, the relative proportions of the fatty acids differed among tissues. Selective incorporation of C16:1 clearly occurred. For each diet group, the fatty acid composition of the epididymal fat pad adipose tissue was more closely similar to that of the diet than was any other tissue examined. This finding is consistent with the fact that chylomicrons derived from dietary fat are a chief source of the fatty acids incorporated into adipose tissue. The POL group fat pad was greatly enriched in C16:1 compared to the other dietary groups.

Interestingly, the HF diet rats had a small percentage of C16:1 in their fat pads and other tissues even though the diet provided none. The OLO diet rats also had a greater proportion of C16:1 in the fat pads than was present in the diet. These findings indicate that the animals synthesize their own C16:1 when dietary sources are inadequate. In addition, they may selectively sequester C16:1 in tissues as needed. The average content of C16:1 found in a particular tissue when animals have been fed for several weeks on a diet essentially devoid of C16:1 therefore may be used to define a mean basal level of C16:1 in such tissue for animals of that species. As is apparent from Table IV, the mean basal level of C16:1 varies among tissues and certainly is expected to vary according to the species of animal analyzed.

In addition to changes in the proportions of fatty acids present in adipose tissue, the various diets caused changes in the total weight of fatty acid triglycerides present per unit weight of adipose tissue. The POL group rats averaged 697 mg total fatty acids/g fat pad tissue; the OLO group rats, 662 mg/g; and the HF group rats, 951 mg/g. Thus both monounsaturated diets produced lower triglyceride content per unit weight than did the saturated fat diet. This result is consistent with the fact that lipases require fluid triglyceride substrates: the saturated HF triglycerides would be hydrolyzed more slowly than the lower melting monounsaturate enriched triglycerides produced by the POL and OLO diets. These results indicate that a diet containing elevated amounts of short chain MUFAs is useful for reducing the triglyceride content of adipose tissue fatty deposits. This property of short chain MUFAs is expected to be beneficial in promoting fat mobilization to reduce adipose tissue deposits, when accompanied by restricted caloric intake.

In the liver, the POL group had more than twice as much C16:1 as did the HF group and four times as much as did the OLO group on a percent by weight basis. Both the POL and OLO groups accumulated more total fatty acids per unit weight of liver than did the HF group: 42.4 mg/g tissue for POL, 42.7 mg/g tissue for OLO, and only 33.2 mg/g tissue for HF. The lower fat content of HF livers suggested that these livers might be healthier than the fattier livers of the POL and OLO diet groups. However, analyses for plasma levels of liver-related enzymes and metabolites, reported in Table VI, did not support this inference.

tase (APH). APH levels are slightly above the mean but well within the normal range for all three groups. Together, these plasma enzyme levels do not indicate that liver cells were pathologically stressed in any of the diet groups. They do suggest that the liver cells were metabolizing a greater amount of lipid rather than glucose for energy and that the POL group animals were somewhat more active in lipid metabolism than the other groups.

Another indicator of the functional health of the liver is the plasma protein concentration, and especially the albumin concentration. Synthesis and secretion of these plasma proteins is a major function of the liver. Both total protein (TPR) and albumin (ALB) values were within normal ranges for all three groups, indicating adequate liver function. The albumin-to-globulin (A/G) ratio was high normal in the POL and HF groups, and slightly above normal in the OLO group. Since albumin concentrations were low normal for all groups, this suggests that globulin levels also must have been low normal for POL and HF groups, and possibly below normal for the OLO group.

Finally, plasma bilirubin (BIL) levels were normal in all groups, indicating no biliary obstruction or severe liver disease.

Liver tissue samples from all eighteen rats were ex-

TABLE VI

| | Plasma Levels of Enzymes, Proteins and Metabolites Indicative of Liver and Kidney Function | | | | | | | | | |
|---|---|---|---|---|---|---|---|---|---|---|
| | GPT | GOT | APH | TPR | ALB | A/G | BIL | URI | CRT | BUN |
| | (unit/L) | | | (g/dL) | | | (mg/dL) | | | |
| POL | 49 | 221 | 374 | 5.9 | 3.3 | 1.25 | 0.3 | 1.8 | 0.4 | 15 |
| HF | 48 | 200 | 335 | 6.0 | 3.3 | 1.20 | 0.3 | 1.4 | 0.4 | 16 |
| OLO | 53 | 195 | 340 | 6.1 | 3.5 | 1.35 | 0.2 | 1.5 | 0.4 | 16 |
| Normal Rat | | | | | | | | | | |
| Upper | 107 | 192 | 525 | 7.1 | 4.5 | 1.30 | 0.6 | 3.7 | 0.4 | 28 |
| Lower | 21 | 64 | 100 | 5.5 | 3.1 | 0.7 | 0.1 | 1.1 | 0.1 | 9 |
| Mean | 64 | 128 | 313 | 6.3 | 3.8 | 1.0 | 0.4 | 2.4 | 0.3 | 14 |

These results indicate that levels of significant liver enzymes which may become elevated in plasma secondary to liver cell injury were not uniformly raised, as would be expected if cellular damage were responsible. For example, levels of glutamatepyruvate transaminase (GPT) were low normal in all three groups compared to the historical norms for male rats in the clinical analyzer employed. This lowered level may reflect the fact that pyruvate is produced by glycolysis, and is therefore elevated when glucose is the primary nutrient being metabolized for energy. Conversely, pyruvate is present in lesser concentrations when lipids are the predominant energy source. GPT therefore is not needed as much when lipids are being metabolized rather than glucose. This rationale also may explain the observed elevation in the plasma levels of the liver enzyme glutamateoxaloacetate transaminase (GOT). GOT levels were slightly above the normal range for all three groups, with the POL rats measuring about 10% higher than the OLO and HF rats. Along with other Krebs cycle intermediates, oxaloacetate concentrations are elevated when lipids are metabolized for energy, because lipid oxidation produces large amounts of acetyl Co-A which then enters the Krebs cycle. Since this acetyl Co-A load causes elevated oxaloacetate levels, the synthesis of GOT should be induced as well. The slightly higher GOT level among POL group rats therefore may reflect a higher rate of metabolism of lipids for energy in that group. A third plasma enzyme which may be spilled from the liver is alkaline phosphaamined under the microscope. Mediastinal tissues including liver were fixed in paraffin, sectioned, and stained with hematoxylin and eosin. Histologial examination of the thoracic tissue revealed striking differences among the groups. Despite the high fat intake and measured fatty acid content of the POL group rats, their livers evidenced no lipid accumulation within the hepatocytes. The hepatocyte density, or number of cells per high-powered field of view (HPF) was normal, indicating compact and healthy cells. In addition, the adjacent extrahepatic mediastinal tissues showed no evidence of fat deposits. All six POL group animals exhibited these characteristics. These observations led the pathologist conducting the histological examination under double blind conditions to label the POL animals a "lean" group.

By contrast, the mediastinal tissues of HF diet animals exhibited numerous hepatocytic foci of high fat accumulation. Many fat cells were swollen with intracellular triglyceride deposits. In consequence, cell density (hepatocytes per HPF) was decreased compared to the POL group animals. Also, the extrahepatic mediastinal tissues showed some increased lipid accumulation compared to the POL group. The pathologist labelled the HF animals as a "moderate fat gain" group.

The tissues of the OLO group animals exhibited even higher lipid accumulation within hepatocytes and the beginning of frank cellular fatty changes. Fat accumulation was diffuse rather than focal as in the HF group. Hepatocyte density was low. In addition, the extrahepatic mediastinal structures showed the greatest increase in accumulated lipids. The pathologist characterized the OLO animals as a "heavy fat gain" group.

Together, these dramatic differences indicate an important and unanticipated benefit from the presence of short chain MUFAs in the diet: they can prevent or reduce the development of fatty liver in animals exposed to conditions which promote fatty liver. In the present study, the high fat and excessive calorie diet itself was the predisposing condition. Other known predisposing factors include exposure to chlorinated solvents or similar toxic chemicals, heavy alcohol ingestion, viral hepatitis, or exposure to certain metabolic inhibitors (e.g., orotic acid) which interfere with the hepatocytic intracellular processing and secretion of VLDL. All of these agents produce fatty liver by causing the rate of input of fatty acids into hepatocytes to exceed the rate of processing of fatty acids. Processing of fatty acids within the liver includes both energy-producing metabolism of fatty acids to acetyl Co-A, and the synthesis of triglycerides and their secretion as VLDL. From the present data we cannot deduce whether the mechanism by which short chain MUFAs protect hepatocytes involves primarily improved fatty acid metabolism or enhanced VLDL secretion. One mechanism underlying the protective effect of short chain MUFAs apparently is to lessen the tendency of accumulated triglycerides within vesicles to aggregate into large, visible deposits. The healthy livers of the POL group rats contained as much fatty acid per gram of tissue as did the obviously fatty livers of the OLO rats. However, in the healthy POL animals the short chain MUFA C16:1 constituted a much larger fraction of the total fatty acid content. The more fluid lipids of the POL animals apparently remained in small, physiologically functional vesicles, whereas the less fluid lipids of HF and OLO animals aggregated into large intracellular droplets. Since the dietarily derived short chain MUFA concentration in the liver increased sufficiently to alter the fluidity characteristics of liver triglycerides in the protected animals, we anticipate that the beneficial effect of preventing or reducing the development of fatty liver will occur regardless of which specific short chain MUFA is employed.

In addition, the reduction in mediastinal fat deposits observed among POL diet animals is a significant beneficial effect. This may be related to the overall lowering of triglyceride content per unit weight of adipose tissue, as was observed in the epididymal fat pads and discussed previously. Mediastinal fat deposits reflect the occurrence of small patches of adipocytes throughout the thoracic and abdominal cavities. When these adipocytes become laden with triglycerides, the cells expand individually to accommodate the triglyceride deposit. Eventually the adipocyte patch swells sufficiently to become noticeable upon histological examination. Conversely, when triglyceride content is low, the adipocytes shrink individually and the adipocyte patch becomes inconspicuous. The fact that mediastinal fat deposits were not observed in the "lean" POL group rats necessarily indicates the low triglyceride content of the adipocytes. This effect therefore may be another manifestation of the previously discussed propensity of short chain MUFAs for reducing the triglyceride content per unit weight of adipose tissue. However, an additional implication from these shrunken mediastinal fat deposits is that the overall size of the adipose tissue had not increased due to adipocyte proliferation to compensate for the decreased triglyceride concentration. Thus another unexpected benefit of a diet containing high proportions of short chain MUFAs is a reduction in the total size of fat deposits.

A further area in which we have now demonstrated beneficial effects involves the plasma lipoproteins. Results of analyses for plasma triglycerides, total cholesterol, HDL cholesterol, residual (VLDL+LDL) cholesterol, and HDL/LDL ratio are presented in Table VII.

TABLE VII

|  | Triglycerides (mg/dL) | Plasma Lipids | | | |
|---|---|---|---|---|---|
|  |  | Total Cholesterol (mg/dL) | HDL Cholesterol (mg/dL) | VLDL + LDL Cholesterol (mg/dL) | HDL/LDL |
| POL | 240 | 83 | 65 | 18 | 3.9 |
| HF | 280 | 82 | 36 | 46 | 2.8 |
| OLO | 324 | 93 | 62 | 31 | 1.2 |
| Normal Rat |  |  |  |  |  |
| Upper | 183 | 90 |  |  |  |
| Lower | 17 | 60 |  |  |  |
| Mean | 100 | 75 |  |  |  |

Several points stand out. First, the plasma triglyceride levels are unusually elevated for all three groups. This is not surprising given the high levels of consumption of dietary fat. The triglyceride content of plasma reflects mainly the contributions from VLDL. The POL group had the lowest average triglyceride levels, only slightly above the normal range for rats. The OLO group had the highest levels, nearly one-third higher than the POL group. The short chain MUFA diet has an apparent advantage over both the saturated fat and olive oil diets with respect to plasma triglyceride levels.

The total cholesterol levels of all three groups were somewhat above the mean but within the normal range for rats. The three diets were derived from vegetable oils and were essentially cholesterol free, which may have helped to keep the plasma cholesterol levels in check. Here again the POL diet provided somewhat lower levels than did the OLO diet. However, the real advantage of the POL diet becomes apparent when HDL cholesterol levels are considered. The POL diet animals had 5% greater mean HDL cholesterol levels than did the OLO animals. This is quite important, inasmuch as olive oil itself is reported to spare HDL cholesterol levels. The POL diet also produced much higher HDL cholesterol levels than did the HF diet. Since HDLs protect against atherosclerosis, the high HDL levels engendered by the short chain MUFA diet are therefore, in light of this discovery, expected to be of great benefit for humans at risk for atherosclerotic vascular disease.

The fraction of total plasma cholesterol which is not in the HDL pool is necessarily divided between VLDLs and LDLs. When the total and HDL cholesterol results are combined, it is apparent that the POL diet also produced lower levels of (VLDL +LDL) Although the cholesterol contents of VLDL and LDL pools were not determined directly, the triglyceride values indicate that the VLDL levels of the POL group animals are about 25% lower than those of the OLO group. By contrast, the residual (VLDL +LDL) cholesterol levels of the POL group are 44% lower than those of the OLO group. Thus the lower level of VLDL observed for the POL diet cannot explain the entire difference in residual cholesterol values between the POL and OLO diets. Therefore the POL diet must have produced lower LDL cholesterol levels as well. This interpretation is strongly bolstered by the fact that LDL cholesterol levels are normally much higher than VLDL cholesterol, and would be expected to represent most of the combined residual (VLDL & LDL) cholesterol Furthermore, an independent lipoprotein determination confirmed the LDL cholesterol lowering effect of the short chain MUFA diet compared to either the saturated fat or olive oil diets. Plasma samples were subjected to electrophoresis on cellulose acetate strips, then stained with Fat Red 7B dye to visualize the lipoprotein bands. The strips were quantitated by optical scanner to give the relative percentages of each of the lipoproteins HDL, VLDL, and LDL. These percentages are based upon the amount of dye absorbed rather than upon the cholesterol content of the fractions; hence the numerical proportions of each lipoprotein component in a given sample based on absorbed dye content are quite different from the proportions calculated from cholesterol content. However, comparisons between samples are quite meaningful. The HDL/LDL ratio calculated by electrophoresis was 3.9 for the POL group, 2.8 for the HF group, and only 1.2 for the OLO group. This directly demonstrates that the HDL/LDL ratio was increased by the POL diet. In addition, these results indicate that LDL levels were decreased by the POL diet, since the increase in the HDL/LDL ratio is too large to be explained solely by the 5% increase in HDL cholesterol between the POL and OLO groups.

Yet another beneficial effect of the diet containing the DBD composition which has been demonstrated by these experiments is on plasma glucose levels. These are given in Table VIII.

TABLE VIII

| Plasma Glucose Concentration and Amylase Activity | | |
|---|---|---|
| Group | Glucose (mg/dL) | Amylase (units/L) |
| POL | 138 | 279 |
| HF | 135 | 284 |
| OLO | 150 | 332 |
| Normal Rat | | |
| Upper | 197 | 410 |
| Lower | 98 | 102 |
| Mean | 143 | 256 |

The plasma glucose concentrations of all three groups were within the normal range. However, the POL and HF groups gave values 5% and 3% respectively below the normal mean, whereas the OLO group gave values 5% higher than the normal mean. These differences are modest but statistically significant. Moreover, the increased glucose levels observed in the OLO group are ominous in light of the risk of type II diabetes among obese animals consuming a high fat diet. The fact that the plasma glucose levels of the OLO animals had begun to rise after only eight weeks on the high fat diet strongly indicates that they were becoming incipiently diabetic. This inference is supported by the elevation in plasma amylase concentration observed among the OLO animals. Amylase is a complex carbohydrate metabolizing enzyme normally secreted by the pancreas into the small intestine; increased amounts in plasma indicate stressing of or damage to pancreatic cells. The pancreas is also stressed by elevated plasma glucose levels, which require that organ to secrete greater amounts of insulin. The animals fed the OLO diet had a plasma amylase activity 30% higher than the normal means and 19% higher than the animals given the POL diet. These elevated plasma amylase concentrations suggest that the OLO animals experienced some pancreatic stress secondary to their prolonged increase in circulating glucose. The near normal plasma glucose and amylase levels observed for the POL animals demonstrate that they developed no pre-diabetic indicators despite their high fat diet and concomitant obesity. These surprising results support a role for administration of short chain MUFAs to control or prevent type II diabetes.

C. Preparation of oil enriched in short chain MUFAs

Although the oil extracted from macadamia nuts was convenient for animal studies because of its fortuitous similarity to the olive oil used as a control, a formulated oil produced by other means is desirable for many applications. We have produced such oils from animal fat sources by a combination of processing steps. The resulting DBD compositions are distinguishable from the naturally occurring precursors by having greater proportions of selected short chain MUFAs and lower proportions of long chain fatty acids.

Several animal fats contain short chain MUFAs in sufficiently high proportions to make them good starting materials for formulating DBD compositions. Chicken and turkey fats, beef tallow, and neatsfoot oil triglycerides contain C16:1n-7 in amounts of about 4-6% by weight. Some fish oils such as sardine and menhaden may contain as much as 10-16% C16:1n-7. Whale oil is reported to contain above 13% C16:1n-7, and the now unavailable sperm whale oil contained up to 26%. However, these fats and oils as rendered from the natural sources contain undesirably large relative proportions of the long chain fatty acids of the series C20:x and above. The more saturated and higher melting members C20:0, C20:1, C22:0, and C22:1 have been reported to contribute to the high atherogenicity of peanut oil, a phenomenon comprehensible in light of the teachings of this patent. See F. Manganaro, et al., 16 Lipids 508 (1981). The polyunsaturated and lower melting members C20:2, C20:3, C20:4, C20:5, C22:2, C22:3, C22:4, C22:5, and C22:6 are non-atherogenic or even cardioprotective, but are highly sensitive to free radical oxidation and cross linking reactions because of their polyunsaturation.

The sole source of a dietary vegetable oil which contains appreciable amounts of C16:1n-7 is macadamia nuts. The two species, integrifolia and tetrafolia, contain C16:1n-7 in amounts ranging from 16 to 25% (w/w) of the fatty acids in the oil. However, both also contain about 4% C20 fatty acids.

Similarly, some natural fats and oils are acceptable starting materials from which to manufacture DBD, that is, an oil enriched in the other selected short chain MUFAs. For example, tallow contains about 0.5% C14:1n-5. It also contains about 1% or more C20 to C22 fatty acids. Butterfat contains very large proportions, up to 3%, of C14:1n-5. However, butterfat has other undesirable lipid components due to the large fraction of C4 to C10 fatty acids. These are metabolized by a quite different pathway from the C12 and longer fatty acids. Butterfat also contains greater than 2% C20 fatty acids. We have produced a DBD composition in which C14:1n-5 comprises greater than 1% of the fatty acids and the C4 to C10 and C20 to C22 fatty acids are present in much lower levels than in butter or tallow.

EXAMPLE 1

Preparation of C16:1n-7 Enriched Oil

A mixture of lard and tallow triglycerides was used as starting material. The oil was chilled at 4° C. for a period of about 14 days to accomplish crystallization of higher melting triglyceride components. The triglyceride mixture was then filtered at 4° C. through a 200 mesh filter of cloth or paper to remove the solid fat crystals. The filtrate was then chilled to $-9.5°$ C. to induce further crystallization and was refiltered at that temperature. The resulting oil was then distilled at a reduced pressure of about 8 microns Hg and a temperature of about 222° C. The first approximately 2% of distillate was collected separately. The subsequently ensuing distillate was collected into 19 fractions of about 5% each. Over the course of distillation the pressure decreased to about 3 microns. The fatty acid profiles of selected fractions were determined by gas chromatographic analysis. These fatty acid compositions for the distilled triglycerides, for their cold treated filtrates, and for comparable starting material triglycerides are given in Table IX.

of C8:0+C10:0 was only about 0.04% in the distilled fractions, compared to about 4.5% in butterfat.

The distilled triglycerides contained low levels of free fatty acids and were suitable for dietary use. Inasmuch as the inventive composition, DBD, was derived from natural fat sources, a variety of chemically distinct lipid species were present in the distilled oil. For example, the C16:1n-7 fatty acid might form an ester with any of the three alcoholic hydroxyl groups of the glycerol backbone, and the other two positions might be occupied by any fatty acid moiety. The inventive composition is not limited to any particular triglyceride, nor is it confined only to triglyceride esters. Monoalcohol esters such as ethyl esters are also suitable compounds for administration to animals. This invention requires only that the amount of short chain MUFA, regardless of the particular lipid species into which it is incorporated, be sufficiently great.

What is claimed is:

1. A formulated composition for administration to an animal, said composition comprising at least one lipid species containing at least one short chain monounsaturated fatty acid selected from the group consisting of C16:1n-7, C16:1n-6, C16:1n-5, C16:1n-4, C16:1n-3, C14:1n-5, C14:1n-4, C14:1n-3, and C12:1n-3, or salts or esters of said monounsaturated fatty acids, and mixtures thereof, said lipid species present in said composition in amounts sufficient to improve the metabolic processing of lipids within said animal upon systematic administration.

2. The composition of claim 1 wherein the improvement in metabolic processing of lipids comprises preventing or lessening fatty deposits within the liver of said animal.

3. The composition of claim 1 wherein the improvement in metabolic processing of lipids comprises increasing the level of palmitoleic acid or its esters within the heart tissue of said animal.

4. The composition of claim 1 wherein the improvement in metabolic processing of lipids comprises lowering the level of saturated fatty acids or their esters within the heart tissue of said animal.

5. The composition of claim 1 wherein the improvement in metabolic processing of lipids comprises lowering the triglyceride content per unit weight of adipose tissue.

6. The composition of claim 1 wherein the improvement in metabolic processing of lipids comprises in-

TABLE IX

Fatty Acid Compositions of Starting Materials, Cold Treatment Filtrate, And Selected Fractions of Distilled Triglycerides (% by weight)

| Fatty Acid | Starting Material* Tallow | Starting Material* Lard | −9.5° C. Filtrate | Distillate Fractions 2 | Distillate Fractions 4 | Distillate Fractions 7 | Distillate Fractions 14 | Distillate Fractions 17 |
|---|---|---|---|---|---|---|---|---|
| C8:0 | | | | 0.02 | | | | |
| C10:0 | | | | 0.02 | | | | |
| C12:0 | 0.9 | 0.2 | 0.05 | 0.10 | 0.1 | 0.1 | 0.02 | 0.0 |
| C14:0 | 3.7 | 1.3 | 2.7 | 4.3 | 3.8 | 3.2 | 1.9 | 1.3 |
| C16:0 | 24.9 | 23.8 | 18.0 | 20.2 | 20.2 | 18.4 | 16.3 | 13.7 |
| C18:0 | 18.9 | 13.5 | 3.8 | 3.2 | 3.3 | 3.7 | 3.9 | 4.5 |
| C14:1 | 1.0 | — | 0.7 | 1.2 | 1.0 | 1.3 | 0.3 | 0.3 |
| C16:1 | 4.2 | 2.7 | 12.9 | 15.9 | 13.9 | 14.3 | 11.0 | 8.9 |
| C18:1 | 36.0 | 41.2 | 48.2 | 42.3 | 45.5 | 44.7 | 50.2 | 52.2 |
| C18:2 | 3.1 | 10.2 | 12.1 | 11.5 | 11.0 | 11.7 | 14.3 | 15.7 |
| C18:3 | 0.6 | 1.0 | 1.1 | 0.7 | 0.9 | 1.7 | 1.5 | 2.3 |
| C20 and above | ~2.0 | ~2.0 | ~1.0 | <0.5 | <0.5 | <0.5 | <0.5 | <0.5 |

*Literature Values: See J. B. Reeves and J. L. Weihranch, "Composition of Foods: Fats and Oils" Agriculture Handbook No. 8-4, U.S.D.A. (June, 1979 ed.); see also Sherex, "Composition and Constants of Natural Fats and Oils."

These data indicate that the proportion of C16:1 was increased by as much as four to five fold compared to the starting tallow and lard triglycerides. At the same time, the proportion of C20 and C22 fatty acid containing triglycerides fell below 1%. The ratio of C16:1 to C20 and above fatty acids increased from about 2 for the starting material fats to as much as 31 for fraction 2. The proportion of C14:1 increased from no more than about 1% in the starting materials to 1.3% in fraction 7. The ratio of C14:1 to C20 and above fatty acids increased from about 1.7 in the lard and tallow starting material to as much as 2.6 in the distillate. The content creasing the plasma HDL cholesterol concentration compared to the HDL cholesterol concentration obtained when said monounsaturated fatty acid is replaced in the diet with a C18 unsaturated fatty acid.

7. The composition of claim 1 wherein the improvement in metabolic processing of lipids comprises increasing the plasma HDL cholesterol concentration compared to the HDL cholesterol concentration obtained when said short chain monounsaturated fatty acid is replaced in the diet with a C12, C14, C16 or C18 saturated fatty acid.

8. The composition of claim 1 wherein the improvement in metabolic processing of lipids comprises increasing the plasma HDL/LDL cholesterol ratio compared to the HDL/LDL cholesterol ratio obtained when said monounsaturated fatty acid is replaced in the diet with a C18 unsaturated fatty acid.

9. The composition of claim 1 wherein the improvement in metabolic processing of lipids comprises increasing the plasma HDL/LDL cholesterol ratio compared to the HDL/LDL cholesterol ratio obtained when said short chain monounsaturated fatty acid is replaced in the diet with C12, C14, C16 or C18 saturated fatty acid.

10. The composition of claim 1 wherein the improvement in metabolic processing of lipids comprises decreasing the plasma LDL cholesterol concentration compared to the LDL cholesterol concentration obtained when said short chain monounsaturated fatty acid is replaced in the diet with a C12, C14, C16 or C18 saturated fatty acid.

11. A formulated composition for administration to an animal, said composition comprising at least one lipid species containing at least one short chain monounsaturated fatty acid selected from the group consisting of C16:1n-7, C16:1n-6, C16:1n-5, C16:1n-4, C16:1n-3, C14:1n-5, C14:1n-4, C14:1n-3 and C12:1n-3, or salts or esters of said monounsaturated fatty acids, and mixtures thereof, said lipid species present in said composition in amounts sufficient to lower the serum glucose concentration of an animal having insulin-resistant elevated serum glucose concentrations upon systematic administration.

12. The composition of claim 1 or claim 11 wherein the said formulated composition comprises at least one said lipid species in a pharmaceutically acceptable carrier for oral or parenteral administration.

13. The composition of claim 1 or claim 11 wherein the said formulated composition comprises at least one said lipid species in a capsule for oral administration.

14. The composition of claim 1 or claim 11 wherein the said formulated composition comprises at least one said lipid species in a prepared food.

15. The composition of claim 1 or claim 11 wherein the said formulated composition comprises at least one said lipid species in a non-naturally occurring edible oil.

16. A formulated composition for administration to an animal comprising at least one lipid species containing at least one short chain monounsaturated fatty acid selected from the group consisting of C16:1n-6, C16:1n-5, C16:1n-4, C16:1n-3, C14:1n-5, C14:1n-4, C14:1n-3 and C12:1n-3, or salts or esters of said monounsaturated fatty acid, and mixtures thereof, wherein said monounsaturated fatty acids constitute at least about 1.2 percent by weight of the fatty acids present in said formulated composition, and the ratio by weight of the content of at least one of the said monounsaturated fatty acids to the combined content of all C20:x and C22:y fatty acids, where x=0 to 5 and y=0 to 6, is at least about 1:1.

17. The composition of claim 16 wherein the said composition is an edible oil.

18. A formulated composition for administration to an animal comprising at least one lipid species containing the short chain monounsaturated fatty acid C16:1n-7, or salts or esters thereof, wherein said C16:1n-7 constitutes at least about 5 percent by weight of the fatty acids present in said formulated composition and wherein the ratio by weight of said C16:1n-7 content to the combined content of all C20:x and C22:y fatty acids, where x=0 to 5 and y=0 to 6, is at least about 8:1.

19. The composition of claim 18 wherein the said composition is an edible oil.

20. A formulated composition for administration to an animal, said composition comprising at least one lipid species containing at least one short chain monounsaturated fatty acid selected from the group consisting of C16:1n-7, or salts or esters of said monounsaturated fatty acids, and mixtures thereof, said lipid species present in said composition in amounts sufficient to improve the metabolic processing of lipids within said animal upon systematic administration.

21. A method of improving the metabolic processing of lipids in an animal comprising
systematically administering to an animal a composition comprising at least one lipid species containing at least one short chain monounsaturated fatty acid selected from the group consisting of C16:1n-7, C16:1n-6, C16:1n-5, C16:1n-4, C6:1n-3, C14:1n-5, C14:1n-4, C14:1n-3, and C12:1n-3, or salts or esters of said monounsaturated fatty acids, and mixtures thereof, said lipid species present in said composition in amounts sufficient to improve the metabolic processing of lipids within said animal.

22. The method of claim 21 conducted for preventing or lessening fatty deposits within the liver of said animal.

23. The method of claim 21 conducted for increasing the level of any said C16 monounsaturated fatty acid or its esters within the heart tissue of said animal.

24. The method of claim 21 conducted for lowering the level of saturated fatty acids or their esters within the heart tissue of said animal.

25. The method of claim 21 conducted for lowering the triglyceride content per unit weight of adipose tissue.

26. A method of claim 21 conducted for lowering the serum glucose concentration of an animal having insulin-resistant elevated serum glucose concentrations.

27. The method of claim 26 wherein said composition contains macadamia nut or macadamia oil as a source for said monounsaturated fatty acid.

28. The method of claim 21 further comprising first providing said lipid species in a pharmaceutically acceptable carrier or prepared food for oral or parenteral administration.

29. The method of claim 28 wherein said composition contains macadamia nut or macadamia oil as a source for said monounsaturated fatty acid.

30. The method of claim 21 conducted for increasing the plasma HDL cholesterol concentration compared to the HDL cholesterol concentration obtained when said monounsaturated fatty acid is replaced in the diet with a C18 unsaturated fatty acid.

31. The method of claim 30 wherein said composition contains macadamia nut or macadamia oil as a source for said monounsaturated fatty acid.

32. The method of claim 1 conducted for increasing the plasma HDL cholesterol concentration compared to the HDL cholesterol concentration obtained when said short chain monounsaturated fatty acid is replaced in the diet with a C12, C14, C16 or C18 saturated fatty acid.

33. The method of claim 32 wherein said composition contains macadamia nut or macadamia oil as a source for said monounsaturated fatty acid.

34. The method of claim 21 conducted for decreasing the plasma LDL cholesterol concentration compared to the LDL cholesterol concentration obtained when said short chain monounsaturated fatty acid is replaced in the diet with a C12, C14, C16 or C18 saturated fatty acid.

35. The method of claim 34 wherein said composition contains macadamia nut or macadamia oil as a source for said monounsaturated fatty acid.

36. The method of claim 21 wherein said composition contains macadamia nut or macadamia oil as a source for said monounsaturated fatty acid.

37. A method of improving the metabolic processing of lipids in an animal comprising
formulating a composition for administration to said animal comprising at least one lipid species containing at least one short chain monounsaturated fatty acid selected from the group consisting of C16:1n-6, C16:1n-5, C16:1n-4, C16:1n-3, C14:1n-5, C14:1n-4, C14:1n-3 and C12:1n-3, or salts or esters of said monounsaturated fatty acid, and mixtures thereof, wherein said monounsaturated fatty acids constitute at least about 1.2 percent by weight of the fatty acids present in said formulated composition, and the ratio by weight of the content of at least one of the said monounsaturated fatty acids to the combined content of all C20:x and C22:y fatty acids, where x =0 to 5 and y=0 to 6, is at least about 1:1; and
systematixally administering said composition to said animal in amounts sufficient to improve the metabolic processing of lipids within said animal.

38. The method of claim 37 wherein said formulated composition comprises said C16:1n-7 acid, or salts or esters thereof, wherein said C16:1n-7 acid constitutes at least about 5 percent by weight of the fatty acids present in said formulated composition and wherein the ratio by weight of said C16:1n-7 content to the combined content of all C20:x and C22:y fatty acids, where x=0 to 5 and y=0 to 6, is at least about 8:1.

39. The method of claim 37 wherein the said composition is an edible oil.

40. The method of claim 38 wherein the said composition is an edible oil.

41. A method of improving the metabolic processing of lipids in an animal comprising
formulating a composition for administration to said animal comprising at least one lipid species containing at least one short chain monounsaturated fatty acid selected from the group consisting of C16:1n-7, or salts or esters of said monounsaturated fatty acids, and mixtures thereof, said lipid species present in said composition in amounts sufficient to improve the metabolic processing of lipids within said animal upon systematic administration; and
systematically administering said composition to said animal in amounts sufficient to improve the metabolic processing of lipids within said animal.

* * * * *